United States Patent
De Vlieger et al.

(10) Patent No.: US 11,485,693 B2
(45) Date of Patent: Nov. 1, 2022

(54) START-UP PROCESS FOR THE PRODUCTION OF GLYCOLS

(71) Applicant: SHELL OIL COMPANY, Houston, TX (US)

(72) Inventors: Dionysius Jacobus Maria De Vlieger, Amsterdam (NL); Pieter Huizenga, Amsterdam (NL); Munro Mackay, Amsterdam (NL); Lucas Petrus Simon Keyzer, Amsterdam (NL); Duraisamy Muthusamy, Houston, TX (US)

(73) Assignee: SHELL USA, INC., Houston, TX (US)

( * ) Notice: Subject to any disclaimer, the term of this patent is extended or adjusted under 35 U.S.C. 154(b) by 40 days.

(21) Appl. No.: 17/275,570

(22) PCT Filed: Sep. 10, 2019

(86) PCT No.: PCT/US2019/050359
§ 371 (c)(1),
(2) Date: Mar. 11, 2021

(87) PCT Pub. No.: WO2020/055831
PCT Pub. Date: Mar. 19, 2020

(65) Prior Publication Data
US 2022/0048838 A1 Feb. 17, 2022

Related U.S. Application Data

(60) Provisional application No. 62/730,569, filed on Sep. 13, 2018.

(51) Int. Cl.
*C07C 29/132* (2006.01)
*B01J 21/18* (2006.01)
*B01J 23/30* (2006.01)
*B01J 23/46* (2006.01)

(52) U.S. Cl.
CPC ............ *C07C 29/132* (2013.01); *B01J 21/18* (2013.01); *B01J 23/30* (2013.01); *B01J 23/462* (2013.01)

(58) Field of Classification Search
CPC ...... C07C 29/132; C07C 31/202; B01J 21/18; B01J 23/30; B01J 23/462
See application file for complete search history.

(56) References Cited

U.S. PATENT DOCUMENTS

| | | |
|---|---|---|
| 2011/0046419 A1 | 2/2011 | Zhang et al. |
| 2011/0312487 A1 | 12/2011 | Chen et al. |
| 2011/0313212 A1 | 12/2011 | Kalnes et al. |
| 2018/0244594 A1 | 8/2018 | Colijn et al. |
| 2018/0326405 A1 | 11/2018 | Edulji et al. |

FOREIGN PATENT DOCUMENTS

| | | |
|---|---|---|
| CN | 102643164 A | 8/2012 |
| CN | 102643165 A | 8/2012 |
| CN | 102675045 A | 9/2012 |
| CN | 103420795 A | 12/2013 |
| CN | 103731258 A | 4/2014 |
| WO | 2012174087 A1 | 12/2012 |
| WO | 2013015955 A2 | 1/2013 |
| WO | 2015154258 A1 | 10/2015 |
| WO | 2016114660 A1 | 7/2016 |
| WO | 2016114661 A1 | 7/2016 |
| WO | 2016180000 A1 | 11/2016 |
| WO | 2018024787 A1 | 2/2018 |

OTHER PUBLICATIONS

International Search Report and Written Opinion received for PCT Patent Application No. PCT/US2019/050359, dated Jan. 7, 2020, 10 pages.
Ji et al., "Direct Catalytic Conversion of Cellulose into Ethylene Glycol Using Nickel-Promoted Tungsten Carbide Catalysts", Angewandte Chemie International Edition, vol. 47, Issue No. 44, Oct. 2008, pp. 8510-8513.
International Search Report and Written Opinion received for PCT Patent Application No. PCT/EP2017/069568, dated Oct. 5, 2017, 8 pages.
Zhang et al., "Kinetic Study of Retro-Aldol Condensation of Glucose to Glycolaldehyde with Ammonium Metatungstate as the Catalyst", AIChE Journal, Nov. 2014, vol. 60, Issue No. 11, pp. 3804-3813.
Liu et al., "Tungsten Trioxide Promoted Selective Conversion of Cellulose Into Propylene Glycol and Ethylene Glycol on a Ruthenium Catalyst", Angewandte Chemie International Edition, vol. 51, Issue No. 13, Feb. 24, 2012, pp. 3249-3253.

*Primary Examiner* — Jafar F Parsa
(74) *Attorney, Agent, or Firm* — Shell USA, Inc.

(57) ABSTRACT

The invention provides a start-up method for a process for the preparation of glycols from a starting material comprising one or more saccharides in the presence of hydrogen and a catalyst system comprising one or more retro-aldol catalysts comprising tungsten and one or more catalytic species suitable for hydrogenation in a reactor, said method comprising introducing the one or more retro-aldol catalysts to the reactor whilst also in the presence of one or more agents suitable to suppress tungsten precipitation.

14 Claims, No Drawings

START-UP PROCESS FOR THE PRODUCTION OF GLYCOLS

CROSS REFERENCE TO RELATED APPLICATIONS

This is a national stage application of International Application No. PCT/US2019/050359, filed 10 Sep. 2019, which claims benefit of priority to U.S. Provisional Application No. 62/730,569, filed 13 Sep. 2018.

The present application claims the benefit of U.S. Provisional Application No. 62/730,569, filed Sep. 13, 2018.

FIELD OF THE INVENTION

The present invention relates to a start-up procedure for a process for the preparation of ethylene and propylene glycols from saccharide-containing feedstocks.

BACKGROUND OF THE INVENTION

Monoethylene glycol (MEG) and monopropylene glycol (MPG) are valuable materials with a multitude of commercial applications, e.g. as heat transfer media, antifreeze, and precursors to polymers, such as PET. Ethylene and propylene glycols are typically made on an industrial scale by hydrolysis of the corresponding alkylene oxides, which are the oxidation products of ethylene and propylene, produced from fossil fuels.

In recent years, increased efforts have focused on producing chemicals, including glycols, from renewable feedstocks, such as sugar-based materials. The conversion of sugars to glycols can be seen as an efficient use of the starting materials with the oxygen atoms remaining intact in the desired product.

Current methods for the conversion of saccharides to glycols revolve around a hydrogenation/hydrogenolysis process as described in Angew. Chem. Int. Ed. 2008, 47, 8510-8513.

A preferred methodology for a commercial scale process would be to use continuous flow technology, wherein feed is continuously provided to a reactor and product is continuously removed therefrom. By maintaining the flow of feed and the removal of product at the same levels, the reactor content remains at a more or less constant volume.

Continuous flow processes for the production of glycols from saccharide feedstock have been described in US20110313212, CN102675045, CN102643165, WO2013015955 and CN103731258. A process for the co-production of bio-fuels and glycols is described in WO2012174087.

Typical processes for the conversion of saccharides to glycols require two catalytic species in order to catalyse retro-aldol and hydrogenation reactions. Typically, the hydrogenation catalyst compositions tend to be heterogeneous. However, the retro-aldol catalysts are generally homogeneous in the reaction mixture. Such catalysts are inherently limited due to solubility constraints. Further, the saccharide-containing feedstock is generally in the form of a slurry in a solvent or as a homogeneous saccharide solution.

The homogeneous tungsten-based catalysts typically used in a saccharides to glycols process may be susceptible to conversion to undesirable products, for example by reduction and precipitation of the metal (tungsten). Precipitated solids in a reactor system can lead to blocked lines and clogging as well as undesirable chemical and/or physical reactions of the tungsten metal with other species present (e.g. catalyst poisoning).

The deposition may occur on any surface, including the walls of the reactor and the surface of the solid hydrogenation catalyst. Over time, this deposition can lead to reduced product yields, operational upsets and reduced catalyst performance.

It is desirable to provide an improved start-up to the process for the conversion of saccharides to glycols in which the deposition of the retro-aldol catalysts is minimized or eliminated.

SUMMARY OF THE INVENTION

The invention provides a method to start-up a process for the preparation of glycols from a starting material including one or more saccharides in the presence of hydrogen and a catalyst system having one or more retro-aldol catalysts and one or more catalytic species suitable for hydrogenation in a reactor, said method including introducing the one or more retro-Aldol catalysts to the reactor whilst also in the presence of one or more agents suitable to suppress tungsten precipitation In some embodiments, a start-up method is described for a process for the preparation of glycols from a starting material including one or more saccharides in the presence of hydrogen and a catalyst system having one or more retro-aldol catalysts including tungsten and one or more catalytic species suitable for hydrogenation in a reactor, said method including introducing the one or more retro-aldol catalysts to the reactor whilst also in the presence of one or more agents suitable to suppress tungsten precipitation.

In another embodiment, a startup process is described for the preparation of monoethylene glycol from a starting material comprising one or more saccharides in the presence of hydrogen and a catalyst system including one or more tungsten based retro-aldol catalysts in a reactor comprising one or more catalytic species suitable for hydrogenation, said process including: introducing one or more agents suitable to suppress catalyst deposition to a reactor; introducing the one or more saccharides to the reactor; and introducing the one or more retro-aldol catalysts to the reactor.

DETAILED DESCRIPTION OF THE INVENTION

The inventors have found that retro-aldol catalyst deposition during the start-up procedure may be prevented by the presence of at least one agent suitable to suppress catalyst deposition in the reactor when the retro-aldol catalyst is introduced into the reactor. The at least one agent suitable to suppress catalyst deposition may be introduced to the reactor prior to the introduction of the retro-aldol catalysts or concurrently with the retro-aldol catalysts.

The start-up process of the present invention may allow for increased lifetime of catalyst and longer operation of the process. In particular, the present invention may minimize or eliminate the retro-aldol catalyst deposition in the start-up process.

The start-up process of the present invention provides that at least one agent suitable to suppress catalyst deposition is present in the reactor along with the retro-aldol catalyst.

In some embodiments, the hydrogenation catalytic composition may be suitably preloaded into the reactor vessel before the reaction is started. The weight ratio of the hydrogenation catalyst composition (based on the amount of metal in said composition) to the potential sugar feed is suitably in the range of from 10:1 to 1:100. Said hydrogenation catalyst composition is preferably heterogeneous and is retained or supported within the reactor vessel. Further, said hydrogenation catalytic composition also preferably comprises one or more materials selected from transition metals from groups 8, 9 or 10 or compounds thereof, with catalytic hydrogenation capabilities.

More preferably, the hydrogenation catalytic composition comprises one or more metals selected from the list consisting of iron, cobalt, nickel, ruthenium, rhodium, palladium, copper, iridium and platinum. The metal or metals may be present in elemental form or as compounds. It is also suitable that this component is present in chemical combination with one or more other ingredients in the hydrogenation catalytic composition. The hydrogenation catalytic composition has catalytic hydrogenation capabilities and is capable of catalysing the hydrogenation of material present in the reactor.

In some embodiments, the hydrogenation catalytic composition comprises metals supported on a solid support. In some embodiments, the solid supports may be in the form of a powder or in the form of regular or irregular shapes such as spheres, extrudates, pills, pellets, tablets, monolithic structures. Alternatively, the solid supports may be present as surface coatings, for example on the surfaces of tubes or heat exchangers. Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

Alternatively, the heterogeneous hydrogenation catalytic composition may be present as a Raney material, such as Raney nickel, preferably present in a pelletised form.

The heterogeneous hydrogenation catalytic composition may require activation after loading in the reactor. Suitable hydrogenation catalyst activation methods are known in the art. Depending on the catalyst, in some embodiments water or another solvent may be circulated to activate the catalyst. In other embodiments, activation of the catalyst may not be necessary.

In some embodiments, after the hydrogenation catalyst has been activated, the startup-process may proceed by continuously feeding one or more agents suitable to suppress catalyst deposition to the reactor. As the one or more agents suitable to suppress catalyst deposition are fed to the reactor, the temperature and the pressure of the reactor may be increased. The temperature should ensure the thermal degradation of the agents suitable to suppress catalyst deposition is negligible in the presence of the hydrogenation catalyst during the start-up process. In some embodiments, the start-up temperature may range from about room temperature (20° C.) to about 250° C., preferably less than 160° C. The pressure in the reactor during start-up is suitably at least 1 MPa, preferably at least 2 MPa, more preferably at least 3 MPa. The pressure in the reactor during startup is suitably at most 15 MPa, preferably at most 10 MPa, more preferably at most 8 MPa. In some embodiments, the pressure in the reactor during startup may be in the range from 1 MPa to 15 MPa, from 2 MPa to 10 MPa or from 3 MPa to 8 MPa.

Preferably, the reactor is pressurised to a pressure within these limits by addition of hydrogen before addition of any saccharide starting material and is maintained at such a pressure until all reaction is complete through on-going addition of hydrogen.

In some embodiments, the pH of the reactor during start-up ranges from about 2.5 to about 7. In other embodiments, the pH of the reactor during start-up ranges from about 3.5 to about 5.

In some embodiments, the agents suitable to suppress catalyst deposition are fed to the reactor prior to the introduction of the retro-aldol catalyst and the temperature of the reactor should be maintained below the degradation temperature of the agents suitable to suppress catalyst deposition, or below the reaction temperature. After a sufficient concentration of the agents suitable to suppress catalyst deposition is in the reactor, the retro-aldol catalyst and saccharide feed are fed to the reactor and the temperature of the reactor is increased to reaction temperature. In other embodiments, the temperature is increased to the on-set temperature of degradation of the agents suitable to suppress catalyst deposition prior to the introduction of the retro-aldol catalyst. In still other embodiments, the temperature is increased to the reaction temperature prior to the introduction of the retro-aldol catalyst.

In other embodiments, the agents suitable to suppress catalyst deposition are fed to the reactor concurrently with the retro-aldol catalyst and the saccharide feed, and the temperature of the reactor may be at the reaction temperature upon such addition.

The agents suitable to suppress catalyst deposition should be in sufficient quantities to suppress deposition when the retro-aldol catalyst is introduced to the reactor. The concentration of agents suitable to suppress catalyst deposition during the start-up process depends on many parameters, such as, but not limited to, at least one of feedstock concentration, organic oxygenates in the product concentration, retro-aldol catalyst concentration, pH, temperature, pressure, etc. In some embodiments, the concentration of the agents suitable to suppress catalyst deposition may be equal to the organic oxygenates concentration in the reactor during normal operation of the process which are typically from about 20 to about 40 weight percent. In some embodiments, the organic oxygenates concentration during normal reactor operation will be a combination of the organic oxygenates in the reactor and any organic oxygenates in the agents suitable to suppress catalyst deposition. In some embodiments, lower concentrations of organic oxygenates may be suitable. In other embodiments, higher concentrations of organic oxygenates may be suitable.

Examples of the agents suitable to suppress catalyst deposition may include the saccharide feed or products formed during the process, e.g. sorbitol, MEG, MPG, 1,2-butanediol, glycerol, other sugar alcohols, aldehydes, ketones, carboxylic acids (glycolic acid, lactic acid, acetic acid), etc. In other embodiments, the agents suitable to suppress catalyst deposition may include adipic acid, sodium bicarbonate, sodium hydroxide, sodium adipate, sodium acetate, sodium lactate and sodium glycolate.

In some embodiments, if the one or more agents suitable to suppress catalyst deposition include the saccharide feed and/or the product formed in the reactor, the agents may be fed prior to the retro-aldol catalyst or may be fed concurrently with the retro-aldol catalyst. Examples of the saccharide feed may include or may be derived from at least one saccharide selected from the group consisting of monosaccharides, disaccharides, oligosaccharides and polysaccharides. If the saccharide feed is fed concurrently with the one or more agents suitable to suppress catalyst deposition, the saccharide feed should contain an organic oxygenates concentration equal to normal operation.

In some embodiments, if the one or more agents suitable to suppress catalyst deposition include the saccharide feed, the saccharide feed may be fed prior to the introduction of the retro-aldol catalyst to build up the organic oxygenates concentration to such an extent that organic oxygenates concentration is equal to normal operation. After the normal operation organic oxygenates concentration is reached, the retro-aldol catalyst is added along with the saccharide feed and the temperature increased to the reaction temperature.

Saccharides, also referred to as sugars, carbohydrates or organic oxygenates, comprise monomeric, dimeric, oligomeric and polymeric aldoses, ketoses, or combinations of aldoses and ketoses, the monomeric form comprising at least one alcohol and a carbonyl function, being described by the general formula of $C_nH_{2n}O_n$ (n=4, 5 or 6). Typical C4 monosaccharides comprise erythrose and threose, typical C5 saccharide monomers include xylose and arabinose and typical C6 sugars comprise aldoses like glucose, mannose and galactose, while a common C6 ketose is fructose. Examples of dimeric saccharides, comprising similar or different monomeric saccharides, include sucrose, maltose and cellobiose. Saccharide oligomers are present in corn syrup. Polymeric saccharides include cellulose, starch, glycogen, hemicellulose, chitin, and mixtures thereof.

If the saccharide feed used includes or is derived from oligosaccharides or polysaccharides, it is preferable that it is subjected to pre-treatment before being used in the process of the present invention. Suitable pre-treatment methods are known in the art and one or more may be selected from the group including, but not limited to, sizing, drying, grinding, hot water treatment, steam treatment, hydrolysis, pyrolysis, thermal treatment, chemical treatment, biological treatment. However, after said pre-treatment, the starting material still comprises mainly monomeric and/or oligomeric saccharides. Said saccharides are, preferably, soluble in the reaction solvent.

Preferably, the saccharide feed, after any pre-treatment, comprises saccharides selected from glucose, starch and/or hydrolysed starch. Hydrolysed starch comprises glucose, sucrose, maltose and oligomeric forms of glucose. Said saccharides are suitably present as a solution, a suspension or a slurry in a first solvent.

The first solvent may be water or a C1 to C6 alcohol or polyalcohol (including sugar alcohols), ethers, and other suitable organic compounds or mixtures thereof. Preferred C1 to C6 alcohols include methanol, ethanol, 1-propanol and iso-propanol. Polyalcohols of use include glycols, particularly products of the hydrogenation/retro-aldol reaction, glycerol, erythritol, threitol, sorbitol and mixtures thereof. Preferably, the solvent comprises water.

In some embodiments, when the agents suitable to suppress catalyst deposition include the saccharide feed and are fed prior to the retro-aldol catalyst, the saccharide feed contacts the hydrogenation catalyst to produce an organic oxygenates mix which may be recycled back to the reactor, thus building up the quantity of agents suitable to suppress catalyst deposition in the reactor. After a sufficient concentration of the agents suitable to suppress catalyst deposition is in the reactor, the retro-aldol catalyst is fed to the reactor and the temperature of the reactor is increased to reaction temperature.

In other embodiments, when the agents suitable to suppress catalyst deposition include the saccharide feed and are fed concurrently with the retro-aldol catalyst, there should be a sufficient concentration of the agents (feed) suitable to suppress catalyst deposition. After the addition of the saccharide feed and retro-aldol catalysts, the temperature of the reactor is increased to reaction temperature.

In other embodiments, the agents suitable to suppress catalyst deposition may include buffer agents which are typically used during the process to control the pH. The buffer agents include organic acids and their corresponding conjugated bases with alkali-metal as their counterions. Examples of suitable buffers include, but are not limited to, acetate buffers, phosphate buffers, lactate buffers, glycolate buffers, citrate buffers and buffers of other organic acids. In a preferred embodiment of the invention, the buffers are alkali metal, more preferably potassium, lithium or sodium, even more preferably sodium species. In other embodiments, the agents suitable to suppress catalyst deposition may include organic acids such as, but not limited to, acetic acid, lactic acid, glycolic acid, glyoxylic acid, oxalic acid, acrylic acid, pyruvic acid, malonic acid, propanoic acid, glyceric acid, maleic acid, butanoic acid, methyl melanoic acid, malic acid, tartaric acid, dihydroxytartaric acid, itaconic acid, mesaconic acid, glutaric acid, dimethylmalonic acid, pentanoic acid, citric acid, adipic acid, and hexanoic acid. In some embodiments, the organic acids are those produced in the process and which can be recycled via the organic oxygenates stream.

In some embodiments, the agents suitable to suppress catalyst deposition may include products formed during the process, e.g. sorbitol, MEG, MPG, 1,2-butanediol, glycerol, other sugar alcohols, aldehydes, ketones, acids, etc. These agents may be fed prior to the addition of the retro-aldol catalyst to establish the concentration of the agents suitable to suppress catalyst deposition and once continuous operation is established, may be recycled back to the reactor to maintain the concentration of the agents suitable to suppress catalyst deposition in the reactor.

If the agents are fed prior to the introduction of the retro-aldol catalyst, once there is sufficient concentration of the agents suitable to suppress catalyst deposition in the reactor, the saccharide feed is added to the reactor along with the retro-aldol catalyst.

If the agents are fed concurrently with the introduction of the retro-aldol catalyst, there should be a sufficient concentration of the agents suitable to suppress catalyst deposition in the combined feed to the reactor. In some embodiments, the agents, the saccharide feed and the retro-aldol catalyst are combined prior to entry to the reactor. In other embodiments, the agents, the saccharide feed and the retro-aldol catalyst are fed separately to the reactor. After addition of the retro-aldol catalyst, the reactor conditions are changed to achieve a steady state concentration of product in the reactor.

Said retro-aldol catalyst composition preferably comprises one or more compound, complex or elemental material comprising tungsten, molybdenum, vanadium, niobium, chromium, titanium or zirconium. More preferably the retro-aldol catalyst composition comprises one or more material selected from the list consisting of tungstic acid, molybdic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides, vanadium oxides, metavanadates, chromium oxides, chromium sulfate, titanium ethoxide, zirconium acetate, zirconium carbonate, zirconium hydroxide, niobium oxides, niobium ethoxide, and combinations thereof. The metal component is in a form other than a carbide, nitride, or phosphide. Preferably, the retro-aldol catalyst composition comprises one or more compound, complex or elemental material selected from those containing tungsten or molybdenum.

In some embodiments, the retro-aldol catalyst is a tungsten-based retro-aldol catalytic species and an alkali metal containing species in a second solvent, making up a retro-aldol stream.

The second solvent is preferably selected from C1 to C6 alcohols or polyalcohols (including sugar alcohols), ethers, and other suitable organic compounds or mixtures thereof. Polyalcohols of use include glycols, particularly products of the hydrogenation/retro-aldol reaction, glycerol, erythritol, threitol, sorbitol and mixtures thereof.

The alkali metal in the alkali metal containing species is preferably lithium, sodium or potassium, more preferably sodium. Further, the alkali metal containing species is preferably present as or derived from a buffer, and/or any other component used to control or modify pH, and/or the tungsten-based retro-aldol catalytic species present in the reactor system.

The retro-aldol stream is at a temperature in the range of from 150° C. to 250° C. Preferably, the temperature of the retro-aldol stream is no more than 230° C. Preferably, the temperature of the retro-aldol stream is at least 160° C. In one preferred embodiment the retro-aldol stream is maintained at a temperature of no more than 10° C. below the temperature in the reactor system.

The weight ratio of the metal-based retro-aldol catalytic species (based on the amount of metal in said composition) to sugar in the combined feed stream is suitably in the range of from 1:1 to 1:1000.

The molar ratio of alkali metal:metal in the combined feed stream is maintained in the range of from 0.55 to 6.0. Preferably, the molar ratio of alkali metal:metal in the combined feed stream is maintained in the range of from 0.55 to 3.0, more preferably in the range of from 1.0 to 2.0.

Hydrogen is also present in the reactor with the retro-aldol catalytic composition.

The present invention is further illustrated by the following Examples.

EXAMPLES

Start-up procedures for saccharide to glycol production were studied using a 100 ml autoclave reactor which has options to simultaneously feed liquid and gas to the reactor. A filter in the autoclave is used to control the liquid level at 50% of the total autoclave volume.

Comparative Example 1: Tungsten Precipitation in Absence of Organics

The reactor was loaded with 0.5 gram of 1.2 wt % Ru/C (on RX3-extra support) (30-80 mesh) hydrogenation catalyst was loaded in the reactor. The catalyst was reduced in the reactor for 1 hr at 300° C. under a H2 flow (3 NL/min) at atmospheric pressure (no liquid present). When the catalyst reduction was completed, the temperature was decreased to 230° C. and the pressure was increased to 100 bar. Water was fed at a rate of 60 g/L to the reactor until steady state operation was obtained. In some embodiments, the stabilization of the pH may indicate steady state operation. The water feed was switched to an aqueous solution containing 1000 ppmwt NaMT, without changing the feedrate of liquid or gas.

The pH stabilized at 6-7 during the water flush. A pH decrease was observed after switching the feed from water to a solution of 1000 ppm NaMT. The liquid product stream that exited the reactor was blue in color. The process ran for 45 hrs before it had to be stopped due to operational issues which were related to blocked product outlet (a pressure drop of 40-50 bars over the product outlet). The reactor was taken down and opened for inspection. It was observed that blue solids in the form of flakes were located on the wall and other surfaces of the reactor (e.g. baffles and product outlet exit). The side of the flakes which were attached to a surface of the reactor was darker in color than the side that was facing the reactor content. Scanning electron microscopy coupled with dispersive X-ray spectroscopy (SEM-EDX) and X-ray photoelectron spectroscopy (XPS) performed on the flakes showed that the flakes were tungsten oxide, with the dark side being more deficient in oxygen. Tungsten was mainly present in its highest oxidation state of 6+. The concentration of sodium in these flakes was found to be very low (atomic ratio W/Na for light blue is ~85, and for dark blue is ~70), related to the sodium metatungstate solution that was fed (Atomic ratio W/Na=2).

Comparative Example 2: Tungsten Precipitation in Absence of Organics

A similar experiment was conducted as described in Example 1, but the hydrogenation catalyst was removed from the reactor and the catalyst activation step was omitted.

Similar results and observations were obtained as in Comparative Example 1. It is hypothesized, without being bound by theory, the blue colored liquid product is an indication that reduction of NaMT occurred as it is reported that the first reduction steps of tungstate yields a blue colored complex 1 (https://www.itia.info/assets/files/newsletters/Newsletter_2013_06.pdf). Comparative Examples 1 and 2 shows that reduced W-species remained partially in solution but also deposit as blue flakes in the reactor.

Example 3: Stabilization of Tungsten in Solution

The reactor was loaded with 0.5 gram of 1.2 wt % Ru/C (RX3-extra) (3-80 mesh) hydrogenation catalyst. The catalyst was reduced in the reactor for 1 hr at 300° C. under a H2 flow (3 NL/min) at atmospheric pressure (no liquid present). When the catalyst reduction was completed, the temperature was decreased to 230° C. and the pressure was increased to 100 bar. Water was fed at a rate of 60 g/L to the reactor until steady state operation was obtained. The water feed was switched to an aqueous reaction solution containing 1 wt % glucose, 2000 ppmwt NaMT, and 450 ppm NaHCO3 (pH controlling agent to run at same pH as Examples 1 and 2) without changing the feedrate of liquid or gas. These conditions were similar (except for the glucose and buffer in the feed) as the experiments described in Comparative Examples 1 and 2.

The reaction ran for 115 hrs. The pH stabilized at ~5 when the flushing with water was completed. A decrease of pH was observed after switching to the aqueous reaction solution. The pH stabilized around a pH of 4.2. No significant pressure drop was observed over the product outlet exit and the liquid product stream was colorless and transparent during the entire run. It was decided to stop the experiment after 114 hrs runtime to inspect the reactor for W precipitation. No W precipitation or carbon deposits were observed in the reactor after the experiment. Typical product yields (based on HPLC analysis) are shown in Table 1.

TABLE 1

| | | | | | | | Glucose |
|---|---|---|---|---|---|---|---|
| | | | | Yield (%) | | | conv. |
| Runtime hrs | MEG | MPG | 1,2-BDO | Sorbitol | Erythritol Threitol | Glycerol | Total glycols* | (%) |
| 29 | 56.9 | 4.8 | 1.2 | 3.2 | 4.9 | 2.6 | 62.9 | 99.7 |
| 68 | 56.4 | 4.7 | 1.3 | 2.4 | 4.9 | 2.2 | 62.4 | 99.9+ |
| 114 | 57.2 | 5.1 | 1.4 | 1.5 | 13.1 | 1.8 | 63.7 | 99.9+ |

*Total glycols = MEG + MPG + 1,2BDO

Upon inspection of the reactor, no blue flakes were formed under the experimental conditions of Example 3 when the NaMT was fed to the reactor in the presence of organics and buffer. Comparative Examples 1 and 2 were conducted under similar reaction conditions as Example 3, but in absence of agents suitable to suppress catalyst deposition, leading to W precipitation in the reactor The product stream of Example 3 was colorless and transparent during the experiment with organic oxygenates and buffer, in contrast to the blue colored product stream observed in Comparative Examples 1 and 2 that were performed in the absence of agents suitable to suppress catalyst deposition during the start-up process. Without being bound by theory, the W-species in solution were stabilized against precipitation by the presence of agents suitable to suppress catalyst deposition.

Comparative Examples 1 and 2 demonstrated that W deposition occurs in absence of agents suitable to suppress catalyst deposition. Without being bound by theory, having agents suitable to suppress catalyst deposition present suppresses W precipitation as shown by Example 3.

It is postulated, without wishing to be bound by theory, that the presence of agents suitable to suppress catalyst deposition in the reactor prior to the introduction of the retro-aldol catalyst prevents the deposition of the retro-aldol catalyst. Precipitation in the reactor could result in operational issues (e.g. clogging) or uncontrollable chemistry in the reactor (Side reactions catalyzed by the precipitated tungsten).

One of the implications is that during start-up of the glycol process, the presence of agents suitable to suppress catalyst deposition will suppress the deposition of the retro-aldol catalyst. By utilizing the described start-up process, catalyst deposition is suppressed, thus providing longer run times and better control of the process.

What is claimed is:

1. A start-up method for a process for the preparation of glycols from a starting material comprising one or more saccharides in the presence of hydrogen and a catalyst system comprising one or more retro-aldol catalysts comprising tungsten and one or more catalytic species suitable for hydrogenation in a reactor, said method comprising the steps of:
   a) activating a hydrogenation catalyst composition in the reactor;
   b) introducing an agent suitable for suppressing tungsten precipitation to the activated hydrogenation catalyst composition in the reactor;
   c) introducing a retro-aldol catalyst to the reactor containing the activated hydrogenation catalyst and the agent, wherein the one or more retro-aldol catalysts comprise at least one of silver tungstate, sodium metatungstate, ammonium metatungstate, sodium polytungstate, tungstic acid, alkali and alkaline earth metal tungstates, alkali and alkaline earth phosphotungstates, phosphotungstic acid, mixed tungstates and molybdates, and silicotungstic acid; and
   d) introducing the starting material to the reactor for preparing a glycol, wherein tungsten precipitation is suppressed during reaction of the starting material.

2. The method according to claim 1, wherein the agent comprises at least one of organic oxygenates or buffer systems comprising one or more organic acids, their corresponding conjugated bases with alkali-metal as their counterions, and mixtures thereof.

3. The method according to claim 2, wherein the agent comprises at least one of organic oxygenate solvents, the starting material, glycols, sugar alcohols, carboxylic acids, other products formed during the process, and mixtures thereof.

4. The method according to claim 2, wherein the buffer systems comprise at least one of acetate buffers, phosphate buffers, lactate buffers, glycolate buffers, citrate buffers or buffers of other organic acids.

5. The method according to claim 1, wherein when the agent is selected from the group consisting of sorbitol, lactic acid, glycolic acid, and combinations thereof.

6. The method according claim 1, further comprising raising the reactor temperature to reaction temperature after introducing the retro-aldol catalyst.

7. A startup process for the preparation of monoethylene glycol from a starting material comprising one or more saccharides in the presence of hydrogen and a catalyst system comprising one or more tungsten based retro-aldol catalysts in a reactor comprising one or more catalytic species suitable for hydrogenation, said process comprising:
   a. activating a hydrogenation catalyst composition in the reactor;
   b. introducing an agent suitable for suppressing catalyst deposition to the activated hydrogenation catalyst in the reactor;
   c. introducing a retro-aldol catalyst to the reactor containing the activated hydrogenation catalyst and the agent; and
   d. introducing the starting material to the reactor for preparing monoethylene glycol, wherein catalyst deposition is suppressed during reaction of the starting material.

8. The process according to claim 7, wherein the agent is a portion of the starting material.

9. The process according to claim 7, wherein the reactor temperature is less than 160° C. prior to the introducing the retro-aldol catalyst to the reactor.

10. The process according to claim 7, wherein the agent comprises at least one of organic oxygenate solvents, glycols, sugar alcohols, or buffer systems comprising one or more organic acids, their corresponding conjugated bases with alkali-metal as their counterions, and mixtures thereof.

11. The process according to claim 10, wherein the reactor temperature is at reaction temperature.

12. The process according to claim 7, further comprising activating the one or more catalytic species suitable for hydrogenation prior to introducing the one or more agents.

13. The method according to claim 1, wherein the reactor temperature in step b) is less than 160° C.

14. The process according to claim 7, wherein the agent is selected from the group consisting of sorbitol, lactic acid, glycolic acid, and combinations thereof.

* * * * *